United States Patent
Kamiya et al.

(10) Patent No.: US 6,711,508 B2
(45) Date of Patent: Mar. 23, 2004

(54) METHOD AND APPARATUS FOR ESTIMATING TIRE AIR PRESSURE

(75) Inventors: Kazuhiro Kamiya, Anjo (JP); Yukio Mori, Nagoya (JP); Takaji Umeno, Aichi-ken (JP); Hideki Ohashi, Chiryu (JP); Yuichi Inoue, Tajimi (JP); Takeyasu Taguchi, Nagoya (JP)

(73) Assignees: Aisin Seiki Kabushiki Kaisha, Kariya (JP); Toyota Jidosha Kabushiki Kaisha, Toyota (JP); Denso Corporation, Kariya (JP)

(*) Notice: Subject to any disclaimer, the term of this patent is extended or adjusted under 35 U.S.C. 154(b) by 0 days.

(21) Appl. No.: 09/993,630

(22) Filed: Nov. 27, 2001

(65) Prior Publication Data

US 2002/0095264 A1 Jul. 18, 2002

(30) Foreign Application Priority Data

Nov. 27, 2000 (JP) ........................ 2000-359588

(51) Int. Cl.$^7$ ............................................. G01L 7/00
(52) U.S. Cl. ....................................................... 702/50
(58) Field of Search ......................... 702/50, 138, 148; 73/146; 324/173; 701/41; 303/196

(56) References Cited

U.S. PATENT DOCUMENTS

| | | | | |
|---|---|---|---|---|
| 5,557,552 A | * | 9/1996 | Naito et al. ................ | 702/148 |
| 5,596,141 A | * | 1/1997 | Nishikawa et al. ......... | 73/146.2 |
| 6,064,931 A | * | 5/2000 | Sawada et al. .............. | 701/41 |
| 6,264,292 B1 | * | 7/2001 | Umeno et al. .............. | 303/196 |
| 6,385,553 B1 | * | 5/2002 | Naito et al. ................. | 702/138 |
| 2002/0030481 A1 | * | 3/2002 | Inoue et al. ................. | 324/173 |

FOREIGN PATENT DOCUMENTS

| | | |
|---|---|---|
| JP | 6-297923 A | 10/1994 |
| JP | 8-219920 A | 8/1996 |
| JP | 9-2031 A1 | 1/1997 |
| JP | 2836652 B2 | 10/1998 |

* cited by examiner

*Primary Examiner*—John Barlow
*Assistant Examiner*—Tung S Lau
(74) *Attorney, Agent, or Firm*—Burns, Doane, Swecker & Mathis, LLP

(57) ABSTRACT

The invention provides an apparatus and a method of estimating tire air pressure with high accuracy from vehicle operation at low at high speeds regardless of various elements to be mounted to the vehicle. Estimation of tire air pressure based on a resonance frequency extracted based on a wheel speed signal outputted from a wheel speed sensor corresponding to the respective tire and estimation of tire air pressure based on a dynamic load radius derived based on the wheel speed signal, are used to selectively switch in accordance with a magnitude of a variance value of the resonance frequency at a plurality of time points.

4 Claims, 13 Drawing Sheets

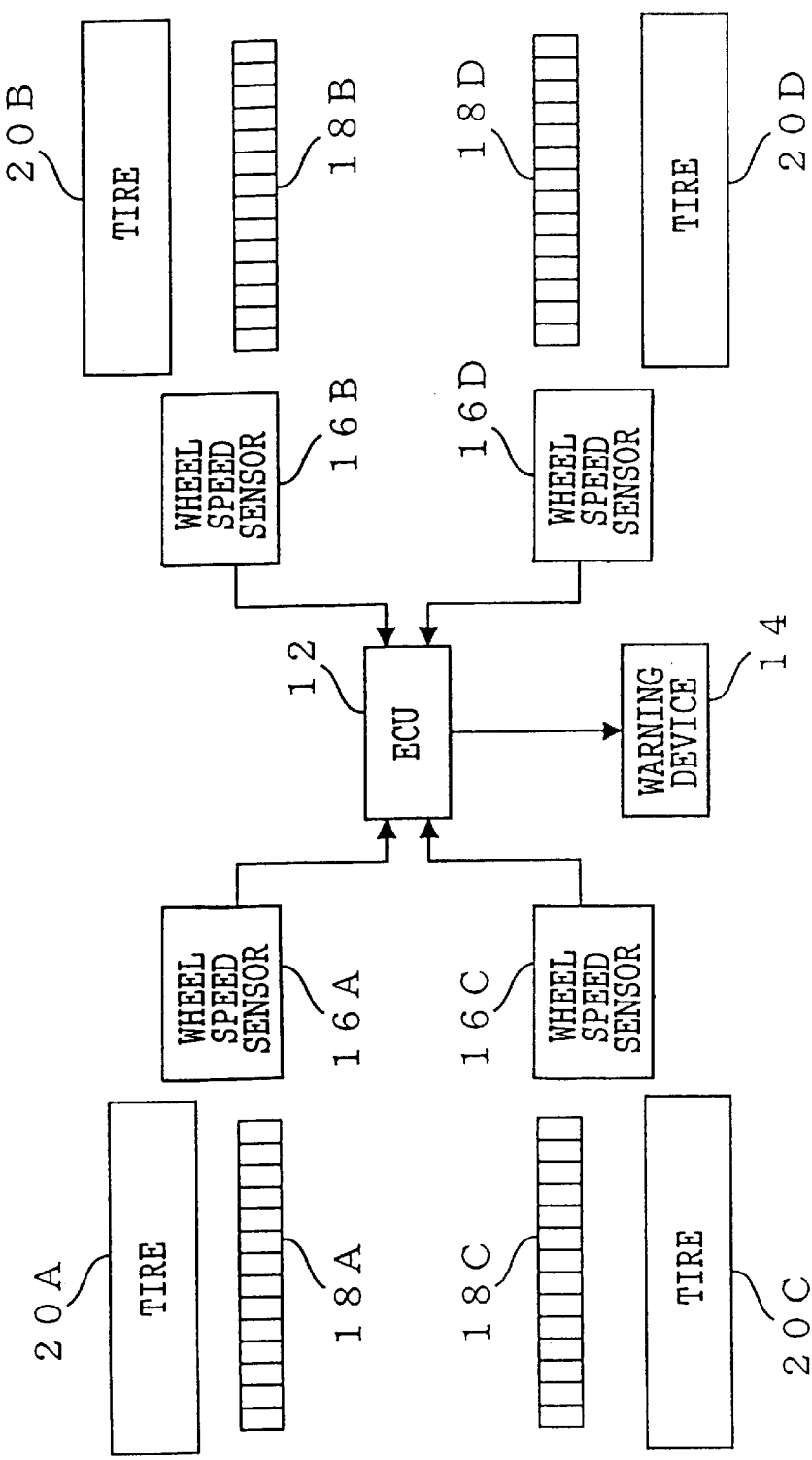

| VARIANCE VALUE $\sigma^2$ | THRESHOLD VALUE Vth (km/h) |
|---|---|
| a | 150 |
| b | 145 |
| c | 140 |
| . | . |
| . | . |
| . | . |

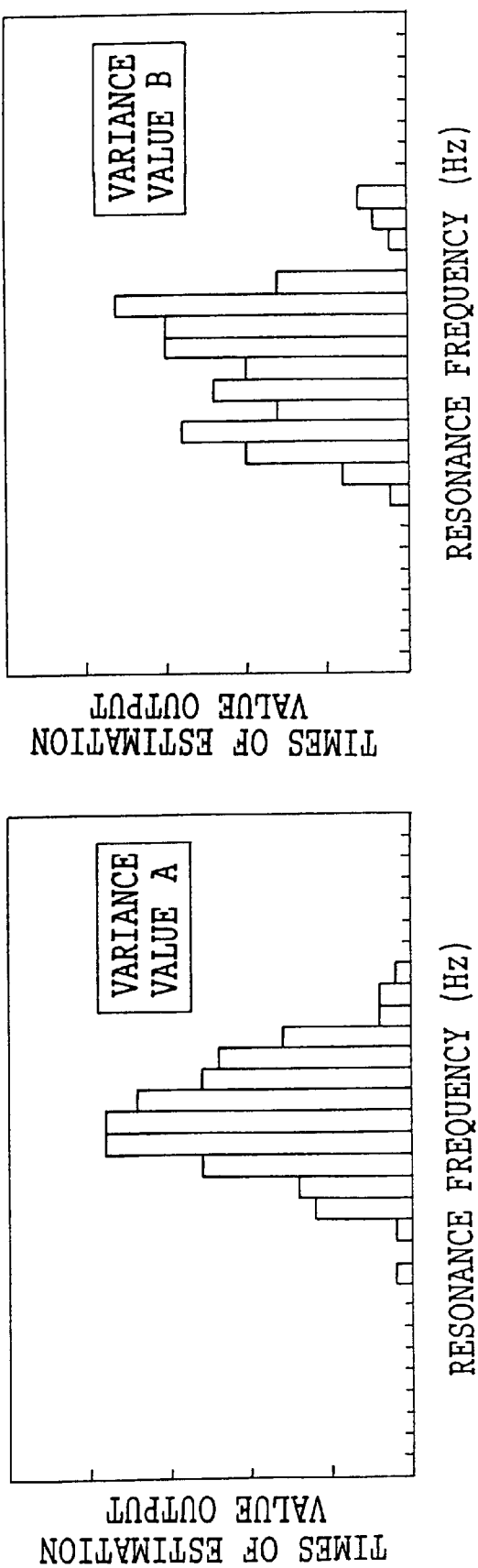

METHOD AND APPARATUS FOR ESTIMATING TIRE AIR PRESSURE

BACKGROUND OF THE INVENTION

1. Field of the Invention

The present invention relates to an apparatus and a method for estimating tire air pressure, and specifically to an apparatus and a method of estimating tire air pressure based on a wheel speed signal.

2. Description of the Related Art

Conventionally, as an apparatus for estimating a state of tire air pressure state, there is a known technology of sampling tire resonance frequency tire by subjecting the wheel speed signal, including frequency components of tire vibration in an operating a vehicle to frequency analysis and detecting tire air pressure state based on the resonance frequency (for example, Japanese Patent Registration No. 2,836,652 and the like).

Resonance frequency within the scope of technology for estimating air pressure in this way, generally falls in a range of about 30 through 50 Hz. However, according to the technology, there is a disadvantage in that there is at least one situation in which tire air pressure cannot be estimated accurately depending on the environment to which the vehicle is subjected as shown below.

FIGS. 9A and 9B show an example of a measurement result of a power spectral level with respect to wheel speed signal. Further, FIG. 9A shows an example of a situation in which vehicle speed is in a mid-range speed of "a" km/h and FIG. 9B shows an example of a situation in which the vehicle speed is in a high range speed of "b" km/h. As shown by the drawings, in a range of a resonance frequency of about 30 through 50 Hz, when the vehicle speed is slow (FIG. 9A), the power spectral level (gain) of the resonance frequency (coupled primary resonance frequency), is high and accordingly, the resonance frequency can be accurately sampled. However, when the vehicle speed is fast (FIG. 9B), the power spectral level of the resonance frequency is low and accordingly, accurate resonance frequency cannot be accurately sampled. This is caused by the fact that when the vehicle is in a high speed region, tire vibration phenomenon has difficulty in occurring.

Therefore, for example, when the vehicle is operating in low to mid speed regions in an urban area, tire air pressure can be estimated with high accuracy in the above-described range of resonance frequency of about 30 through 50 Hz. However, when the vehicle is operating in a high speed region, the power spectral level of the resonance frequency decreases and accuracy for estimating tire air pressure deteriorates.

In order to address this disadvantage, according to technology described in Japanese Patent Application Laid-Open (JP-A) No. 9-2031, there technology proposed for estimating tire air pressure with high accuracy regardless of the vehicle speed by estimating tire air pressure based on the spring constant constituting an index having a high correlation with the resonance frequency when the vehicle speed is slow and estimating tire air pressure based on tire dynamic load radius when the vehicle speed is fast.

According to the technology described in JP-A No. 9-2031, as a condition of switching between the two methods of estimating air pressure, the travel speed of the vehicle is applied. However, the threshold for switching between estimating methods in this case is a fixed determination based on analyzing the vehicle speed when the power spectral level is lowered by experiments or the like. Moreover, the threshold is determined for each of various elements of the vehicle (particularly, tire type). Accordingly, there is a disadvantage in that although estimation accuracy is high for a vehicle corresponding to various elements for which the appropriate threshold has been predetermined, estimation accuracy is low for other vehicles.

SUMMARY OF THE INVENTION

The invention addresses the above-described disadvantage and it is an object thereof to provide an apparatus for estimating tire air pressure with higher accuracy from operation at low to high speeds regardless of the various elements mounted to the vehicle.

In order to achieve the above-described, according to a first preferred embodiment of the invention, there is provided a tire air pressure estimating apparatus comprising an extracting component for extracting a resonance frequency or a spring constant of a tire based on a wheel speed signal including frequency components of vibration of the tire in operating a vehicle, a first estimating component for estimating tire air pressure based on the resonance frequency or the spring constant of the tire extracted by the extracting component, a deriving component for deriving a dynamic load radius of the tire based on the wheel speed signal, a second estimating component for estimating the tire air pressure based on the dynamic load radius derived by the deriving component, and a switching component for selectively switching a estimation of the air pressure by the first estimating component in accordance with a statistic value based on the resonance frequency or the spring constant of the tire at each of a plurality of time points.

The extracting component extracts the resonance frequency or the spring constant of the tire based on the wheel speed signal including the frequency components of vibration of the tire in operating the vehicle. The tire air pressure is estimated by the first estimating component based on the extracted resonance frequency or the extracted spring constant of the tire. As a method of estimating the tire air pressure by the first estimating component, there can be applied all existing methods capable of estimating the tire air pressure based on the resonance frequency or the spring constant of the tire which have estimating methods described in previous publications such as, for example, Japanese Patent Registration No. 2,836,652, JP-A No. 9-2,031, JP-A No. 6-297,923 and JP-A No. 8-219,920.

According to the first embodiment of the invention, the dynamic load radius of the tire is derived based on the wheel speed signal by the deriving component and the tire air pressure is estimated by the second estimating component based on the derived dynamic load radius. As a method of estimating the tire air pressure by the second estimating component, there can be applied all the existing methods capable of estimating the tire air pressure based on the dynamic load radius of the tire such as, for example, a estimating method described in JP-A No. 9-2,031.

Further, according to the first embodiment of the invention, selective switching of estimation of the air pressure by the first estimating component and the second estimating component is performed in accordance with the statistic value based on the resonance frequency or the spring constant of the tire at each of a plurality of time points.

That is, according to the invention, in estimating the tire air pressure, by selectively switching to estimation based on the resonance frequency or the spring constant by the first estimating component having high estimation accuracy when the vehicle is operating at low and mid speeds, and to estimation based on the dynamic load radius by the second estimating component having high estimation accuracy when the vehicle is operating at high speed, regardless of the vehicle travel speed, high estimation accuracy is achieved. As a parameter for switching, the statistic value based on the resonance frequency or the spring constant of the tire in actually operating the vehicle is used. Therefore, regardless of various elements to be mounted to the vehicle, the tire air pressure can be estimated with high accuracy.

In this way, according to the apparatus for estimating tire air pressure of the first embodiment of the invention, estimation of the air pressure by the first estimating component for estimation based on the resonance frequency or the spring constant of the tire, and estimation of the air pressure by the second estimation component based on the dynamic load radius, are used selectively accordance with the statistic value based on the resonance frequency or the spring constant of the tire at each of the plurality of time points. Therefore, regardless of various elements to be mounted to the vehicle, the tire air pressure can be estimated with high accuracy from operation at low to high speeds.

As the statistic value according to the first embodiment of the invention, there can be applied any one of a variance value, a standard deviation value, bias and a kurtosis of the resonance frequencies or the spring constants at the plurality of time points.

FIG. 10A and FIG. 10B show an example of histograms of resonance frequencies at a plurality of time points extracted based on a wheel speed signal. FIG. 10A shows an example of a case in which vehicle speed is a mid speed of "a" km/h and FIG. 10B shows an example of case of in which the vehicle speed is high speed of "b" km/h.

As shown by FIG. 10A, the histogram of the resonance frequency when the vehicle speed is the mid speed of "a" km/h substantially forms a shape of a normal distribution and a variance value of the resonance frequencies in this case has been "A". In contrast thereto, as shown by FIG. 10B, the histogram of the resonance frequency when the vehicle speed is the high speed of "b" km/h, forms an irregular state and a variance value of the resonance frequency in this case has been "B", which is larger than A as mentioned above. As described above, the spring constant of the tire is an index having a high correlation with the resonance frequency. Therefore, a histogram of the spring constant behaves similar to the case for the resonance frequency.

Therefore, by selectively switching between estimation by the first estimating component and the second estimating component in accordance with the variance value of the resonance frequency (spring constant) provided based on the wheel speed signal, the air pressure can be estimated with high accuracy.

Also a standard deviation value having a correlation with the variance value can be dealt with similar to the case of the variance value.

Bias (a degree of shifting the vertex of a normal distribution as shown by FIG. 10A in the left and right directions) or a kurtosis of the resonance frequency (a pointed degree of the normal distribution state as shown by FIG. 10A) can also be considered as the index of representing a degree of accuracy of the extracted resonance frequency. Therefore, also the bias and the kurtosis are applicable as indices for selectively switching of estimation by the first component and second estimating components.

According to a second preferred embodiment of the invention, there is provided a tire air pressure estimating apparatus comprising an extracting component for extracting a resonance frequency or a spring constant of a tire based on a wheel speed signal including frequency components of vibration of the tire in operating a vehicle, a first estimating component for estimating tire air pressure based on the resonance frequency or the spring constant of the tire extracted by the extracting component; a deriving component for deriving a dynamic load radius of the tire based on the wheel speed signal; a second estimating component for estimating the tire air pressure based on the dynamic load radius derived by the deriving component; a wheel speed deriving component for deriving a wheel speed based on the wheel speed signal; a estimation switching component for estimating the tire air pressure by the first estimating component when the wheel speed derived by the wheel speed deriving component is less than a predetermined value and estimating the tire air pressure by the second estimating component when the wheel speed at least equals the predetermined value, and a setting component for setting the predetermined value based on the resonance frequency or the spring constant of the tire.

The resonance frequency or the spring constant of the tire is extracted based on the wheel speed signal including the frequency components of vibration of the tire in operating the vehicle, and based on the extracted resonance frequency or the extracted spring constant of the tire, the tire air pressure is estimated. As a method of estimating the tire air pressure by the first estimating component, similar to the first embodiment of the invention, there can be applied all the existing methods capable of estimating the tire air pressure based on the resonance frequency or the spring constant of the tire, such as estimating methods described in such publications as, for example, Japanese Patent Registration No. 2,836,652, JP-A No. 9-2,031, JP-A No. 6-297, 923 and JP-A No. 8-219,920.

According to the second embodiment of the invention, the dynamic load radius of the tire is derived based on the wheel speed signal. The tire air pressure is estimated by the second estimating component based on the derived dynamic load radius. Also as methods of estimating tire air pressure by the second estimating component, there can be applied all the existing methods capable of estimating the tire air pressure based on the dynamic load radius of the tire such as, for example, a estimating method described in JP-A No. 9-2, 031.

Further according to the second embodiment of the invention, the wheel speed is derived based on the wheel speed signal by the wheel speed deriving component. Using the estimation switching component, operation is switched to estimate the tire air pressure by the first estimating component when the derived wheel speed is less than the predetermined value. Operation is switched to estimate the tire air pressure by the second estimating component when the wheel speed at least equals the predetermined value.

That is, according to the invention, in estimating the tire air pressure, by selectively switching the estimation based on the resonance frequency or the spring constant by the first estimating component having high estimation accuracy when the mounted vehicle is operating at low to mid speeds, and the estimation based on the dynamic load radius by the second estimating component having high estimation accuracy when the mounted vehicle is operating at high speed, regardless of vehicle travel speed, high estimation accuracy is achieved.

Here, According to the invention, by the setting component, the predetermined value for a threshold switching by the estimation switching component, is set based on the resonance frequency or the spring constant of the tire in actually operating the vehicle. Thereby, regardless of various elements of the mounted vehicle, the tire air pressure can be estimated with high accuracy.

In this way, according to the apparatus for estimating tire air pressure of the second embodiment of the invention, operation is switched to estimate the tire air pressure by the first estimating component for estimating the tire air pressure based on the resonance frequency or the spring constant of the tire when the vehicle speed is less than the predetermined value. Operation is switched to estimate the tire air pressure by the second estimating component for estimating the tire air pressure based on the dynamic load radius when the vehicle speed at least equals the predetermined value. The predetermined value is set based on the resonance frequency or the spring constant of the tire and accordingly, regardless of various elements to be mounted to the vehicle, the tire air pressure can be estimated with high accuracy from operating at low speed high speeds.

It is preferable that the setting component according to the second embodiment of the invention, sets the predetermined value in accordance with a statistic value based on the resonance frequency or the spring constant of the tire at each of a plurality of time points. In this case, as the statistic value, by reason similar to that of the first embodiment of the invention, there is applicable any one of a variance value, a standard deviation value, bias and a kurtosis of the resonance frequency or the spring constant at each of the plurality of time points.

In accordance with a third embodiment of the present invention, there is provided a method for estimating tire air pressure. The method includes: (a) extracting a resonance frequency or a spring constant of the tire based on a wheel speed signal including frequency components of vibration of a tire in operating a vehicle; (b) estimating the tire air pressure based on the resonance frequency or the spring constant of the tire extracted; (c) deriving a dynamic load radius of the tire based on the wheel speed signal; (d) estimating the tire air pressure based on the dynamic load radius derived; and (e) selectively switching estimation of the air pressure by step (b) and a estimation of the air pressure using said steps of estimating tire air pressure based on resonance frequency or a spring constant, and the dynamic load radius in accordance with a statistic value based on the resonance frequency or the spring constant of the tire at a plurality of time points.

In accordance with a fourth embodiment of the present invention, there is provided a method for estimating tire air pressure. The method includes:(a) extracting a resonance frequency or a spring constant of the tire based on a wheel speed signal including frequency components of vibration of the tire in operating a vehicle; (b) estimating tire air pressure based on the resonance frequency or the spring constant of the tire extracted; (c) deriving a dynamic load radius of the tire based on the wheel speed signal; (d) estimating the tire air pressure based on the dynamic load radius derived; (e) deriving a wheel speed based on the wheel speed signal; (f) switching from estimation of the tire air pressure by the step of estimating the tire air pressure based on the resonance frequency or the spring constant value when the wheel speed derived is less than a predetermined value and to estimation of the tire air pressure by the step of estimating the tire air pressure based on the dynamic load radius when the wheel speed at least equals the predetermined value; and (g) setting the predetermined value based on the resonance frequency or the spring constant of the tire.

BRIEF DESCRIPTION OF THE DRAWINGS

FIG. 1 is a block diagram showing a tire air pressure estimating apparatus 10 according to a first preferred embodiment;

FIG. 10A is a histogram of resonance frequency provided for an explanation of the principle of the invention in which the vehicle speed is at a middle speed of "a" km/h; and FIG. 10B is a histogram of a resonance frequency provided for an explanation of the principle of the invention in which the vehicle speed is at a high speed of "b" km/h.

DESCRIPTION OF THE PREFERRED EMBODIMENTS

Figure 2A:
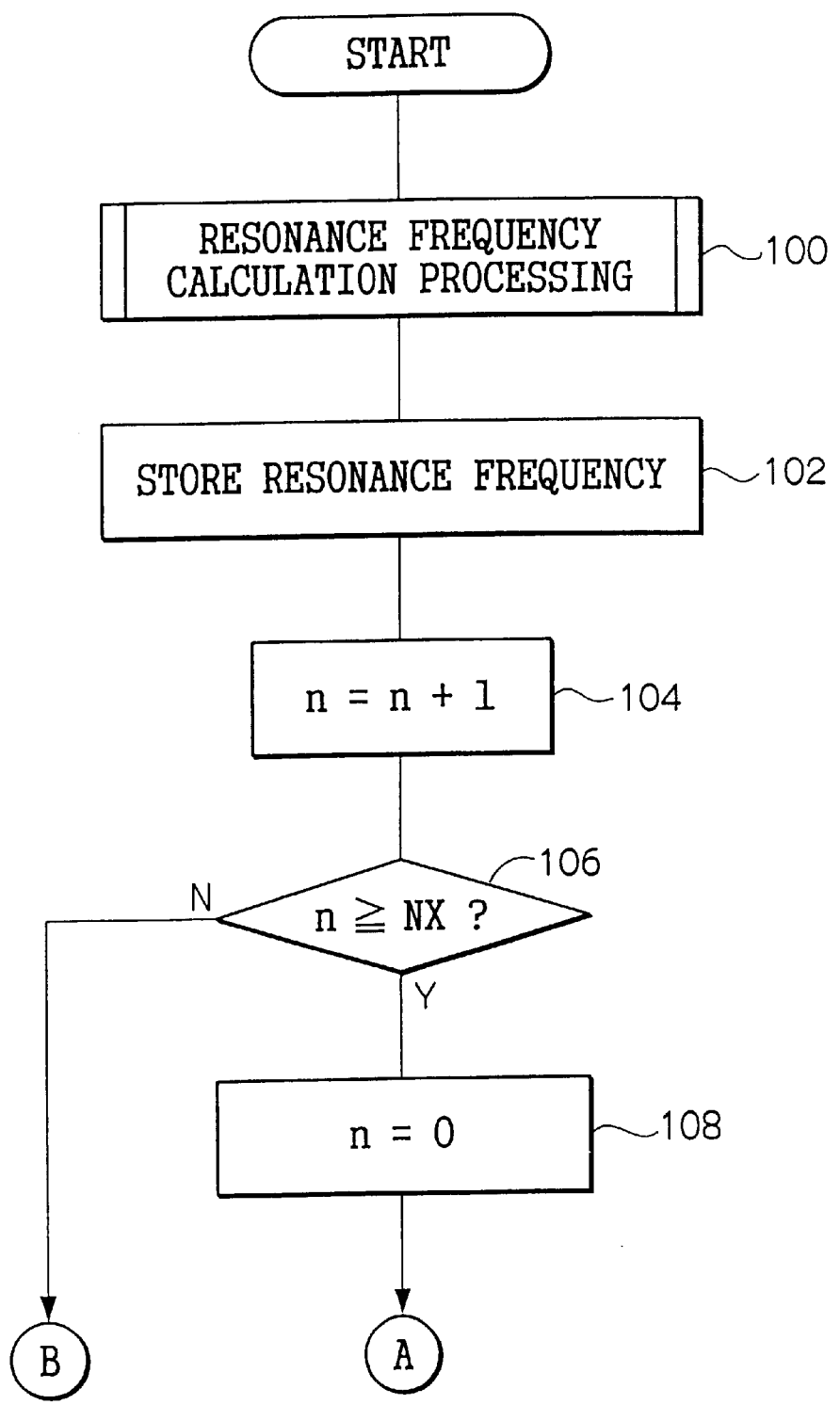
FIGS. 2A and 2B are flowcharts showing a flow for processing in a tire air pressure estimation processing program executed by the tire air pressure estimating apparatus 10 according to the first embodiment.

A detailed explanation will be provided of preferred embodiments of the invention with reference to the drawings as follows.

[First Embodiment]

An explanation will be given of a mode of a first preferred embodiment of the invention. FIG. 1 shows a a tire air pressure estimating apparatus 10 according to the first aspect.

As shown by the drawing, the tire air pressure estimating apparatus 10 according to the first aspect comprises an electronic control device (hereinafter, referred to as "ECU") 12 managing total operation of the tire air pressure estimating apparatus 10, a warning device 14 for providing an alarm under control of the ECU 12, and wheel speed sensors 16A through 16D provided respectively in correspondence with rotors 18A through 18D provided respectively, for tires 20A through 20D of a vehicle.

The respective rotors 18A through 18D include magnetic bodies comprising a circular disk shape and coaxially attached to rotating shafts, not illustrated, respectively corresponding to tires 20A through 20D. Further, the wheel speed sensors 16A through 16D include pickup coils, attached to vicinities of respectively corresponding tires 20A through 20D at predetermined spacing therebetween, and output alternating current signals having periods in accordance with rotational speeds of the rotors 18A through 18D, i. e., the tires 20A through 20D.

Further, output terminals of the vehicle speed sensors 16A through 16D for outputting the alternating current signals are connected to the ECU 12. The ECU 12 includes a microcomputer comprising a CPU, ROM, RAM and the like, and a waveform shaping circuit. The ECU 12 executes predetermined processing including waveform shaping based on the alternating current signals inputted from the respective wheel speed sensors 16A through 16D. Further, the ECU 12, controls give output of a warning by the warning device 14 in accordance with results of the processing.

Figure 2B:
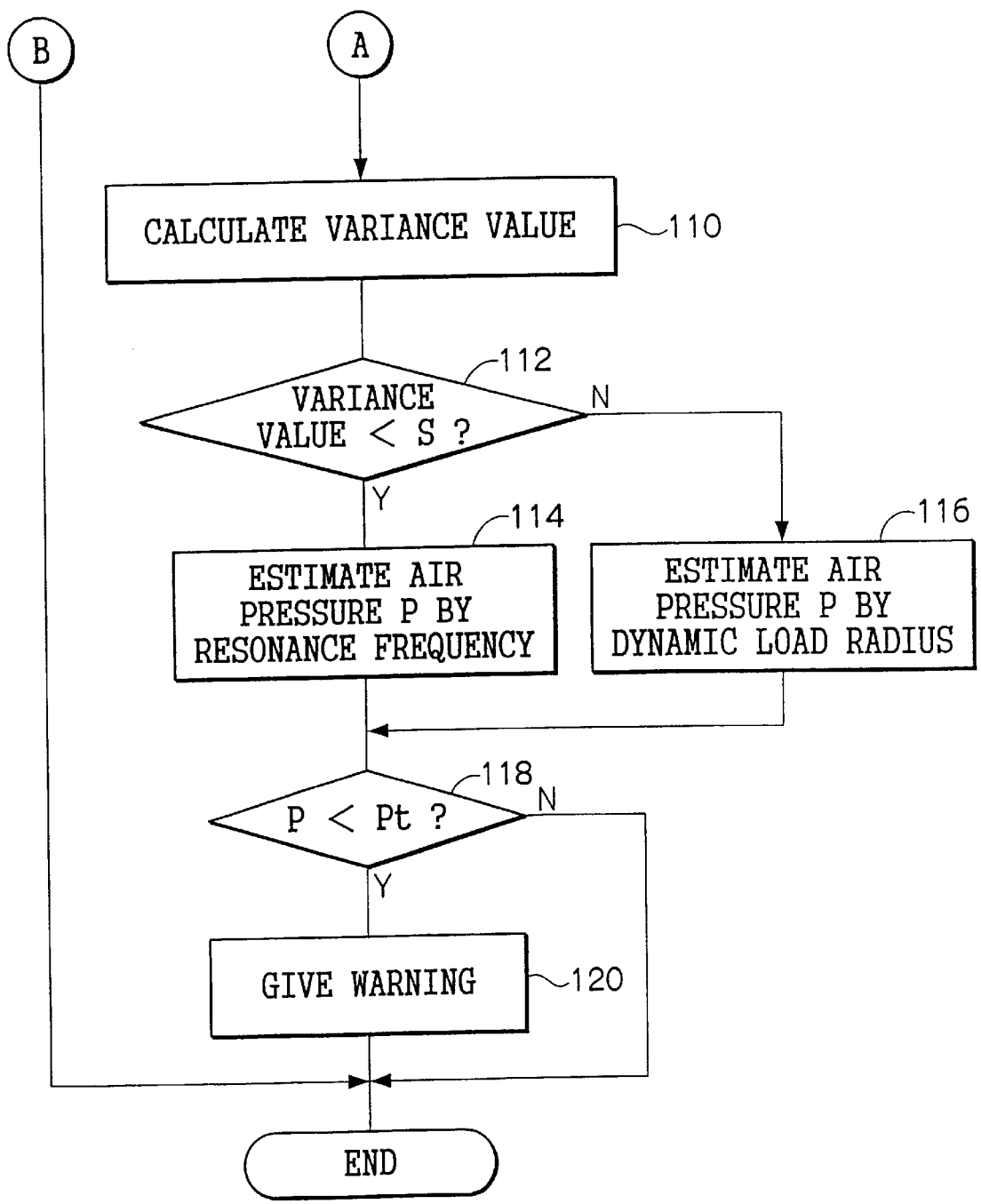

An explanation will be given of operation of the tire air pressure estimating apparatus 10 according to the first aspect with reference to FIGS. 2A and 2B as follows. Further, FIGS. 2A and 2B are flowcharts showing flow of a tire air pressure estimation processing program executed by the CPU of the ECU 12 reiterated at predetermined time intervals, with the program previously stored in the ROM of ECU 12. Further, ECU 12 executes similar processing for the respective tires 20A through 20D and therefore, an explanation will be given here of only the processing for the tire 20A.

Figure 3:
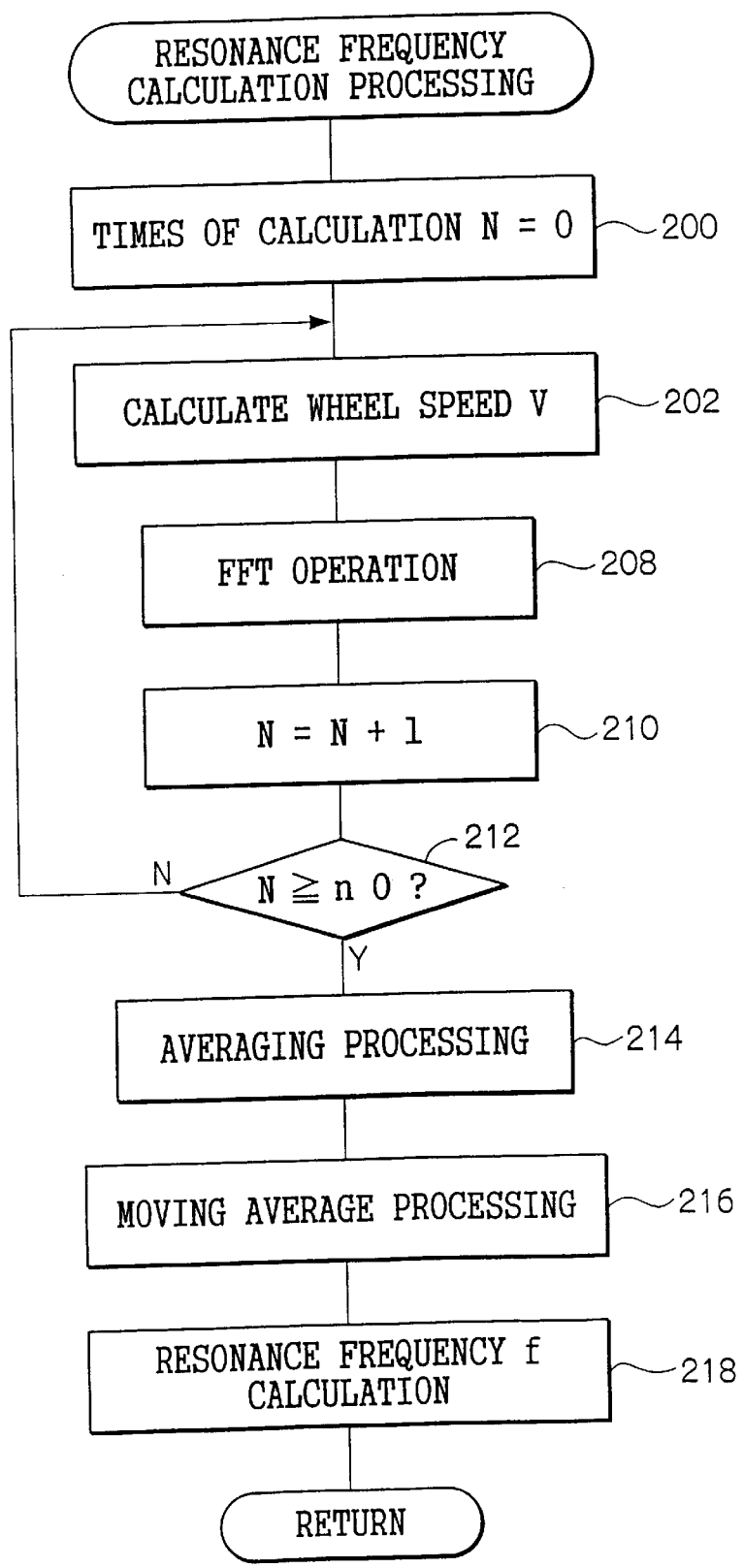
FIG. 3 is a flowchart showing a flow for processing of a resonance frequency operation processing program executed during execution of the tire air pressure estimation processing program.

First, at step 100, resonance frequency operation processing is executed for deriving a resonance frequency based on wheel speed based on the alternating current signal inputted from the wheel speed sensor 16A. An explanation will be given of the resonance frequency operation processing according with in reference to FIG. 3 as follows. In this regard, FIG. 3 is a flowchart showing flow for processing of a resonance frequency operation processing program for executing the resonance frequency operation processing. This program is also stored previously in the ROM of ECU 12.

First, at step 200, an initial setting, 0 (null) is substituted for a variable N representing a number of times of operation of a FFT (Fast Fourier Transformation), mentioned later. At next step 102, the alternating current signal outputted from the wheel speed sensor 16A is subjected to waveform shaping to thereby correspond to a pulse signal. Thereafter, a wheel speed V is calculated based on the time interval between pulses. The wheel speed V normally includes a number of high frequency components including frequency components of tire vibration.

At next step 208, a frequency analysis (FFT) operation is executed for the vehicle speed V calculated at step 202. At next step 210, the variable N is incremented by 1.

Meanwhile, when the FFT operation is executed for a wheel speed provided by actually operating a vehicle on a general road, a very random characteristic normally results. This is because sizes and heights of very small recesses and projections present on the road surface are quite irregular. Hence, the frequency characteristic varies for respective for the wheel speed respectively corresponding these to data. Therefore, according to the aspect, in order to reduce the variation of the frequency characteristic as much as possible, after calculating average values for results of FFT operation at a plurality of times, moving average processing is executed.

Therefore, at next step 212, it is determined whether a value of the variable N representing the number of times of FFT operation at the step 208, reaches a predetermined number of times n0. When the value does not reach the predetermined number of times (i.e., negative determination at step 212), the operation returns to the step 202. And at a time point at which the value reaches the predetermined number of times (time point corresponding to an affirmative determination at step 212), the operation proceeds to step 214 and executes moving average processing. According to the moving average processing, an average value of results of FFT operation at a plurality of times and an average value of gains of the respective frequency components is calculated. By this average processing, variation of the results of FFT operation produced by the road surface can be reduced.

Further, at next step 216, the moving average processing shown below is executed. The moving average processing according to this aspect is executed by calculating an n-th frequency gain $Y_n$ using Equation (1) shown below.

$$Y_n = (Y_{n+1} + Y_{n-1})/2 \qquad (1)$$

That is, according to the moving average processing, the n-th frequency gain $Y_n$ is defined as an average value of an (n+1)-th gain $Y_{n+1}$ in the preceding calculation result and an (n−1)-th frequency gain $Y_{n-1}$ which has been calculated already. The moving average processing results in a waveform in which the result of FFT operation changes smoothly.

At next step 218, based on the FFT operation result smoothed by the moving average processing, a resonance frequency f is calculated for the front and rear direction under the vehicle springs. Thereafter, the resonance frequency operation processing is finished. Further, in this case, the resonance frequency f in the front and rear direction under the vehicle springs is provided by calculating the resonance frequency in a frequency range of about 30 through 50 Hz.

The principle capable of deriving the resonance frequency f based on the result of analyzing the frequency of the signal detected by the wheel speed sensor, is well known as described in Japanese Patent Registration No. 2836652. Therefore, an explanation thereof will be omitted here.

When the resonance frequency operation processing has been finished, the operation proceeds to step 102 of FIGS. 2A and 2B. In particular, the resonance frequency calculated by the resonance frequency operation processing at the step 100, is stored in the RAM of ECU 12 and at next step 104, the value of the variable n is incremented by 1. Further, the variable n represents the number of iterations for calculating the resonance frequency and is set at 0 (null) when the tire air pressure estimating processing is first executed by the tire air pressure estimating apparatus 10.

At next step 106, it is determined whether the value of the variable n is equal to or larger than a predetermined value NX. When the value is not equal to or larger than the predetermined value NX (i.e., a negative determination in step 106), the tire air pressure estimating processing finishes without executing processing thereafter. When the value is equal to or larger than the predetermined value NX (i.e., an affirmative determination in step 106) the operation proceeds to step 108.

At step 108, 0 is substituted for the variable n and at next step 110, a square of a variance of the resonance frequencies $f_i$ (i=1,2, . . . , NX) which have been accumulated in the RAM of ECU 12 until that time, is calculated using Equation (2) shown below.

$$\sigma^2 = \frac{1}{NX} \sum_{i=1}^{NX} (f_i - f_{AVE})^2 \qquad (2)$$

wherein, $$f_{AVE} \left( = \frac{1}{NX} \sum_{i=1}^{NX} f_i \right)$$

is the average value of resonance frequency $f_i$.

Figure 4:
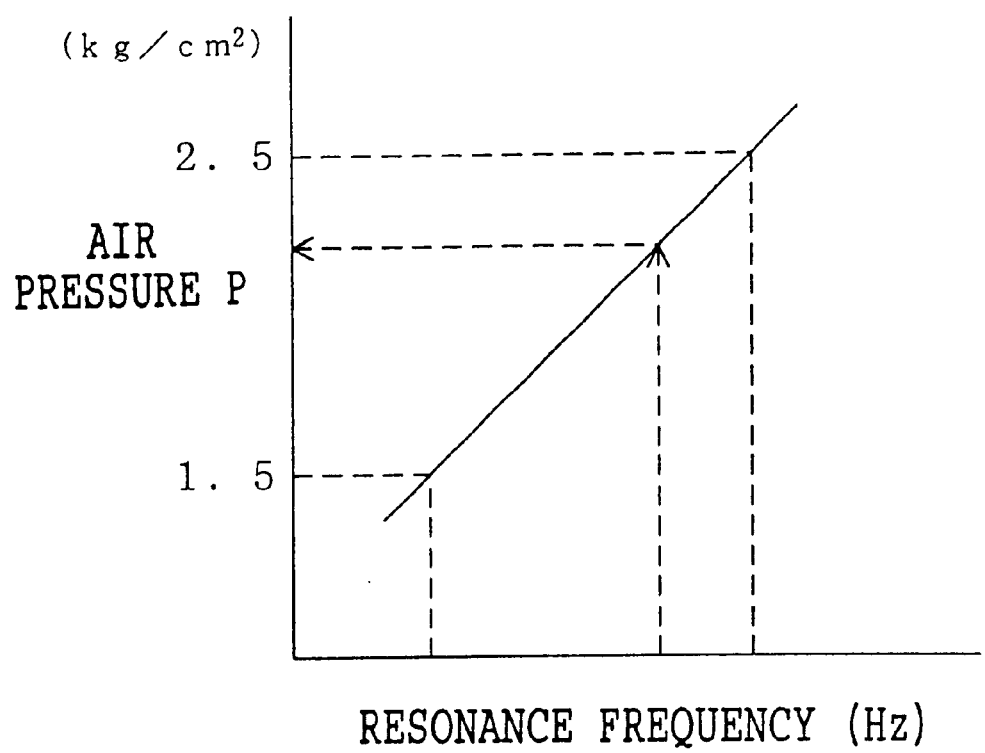
FIG. 4 is a graph showing an example of a relationship between resonance frequency and air pressure.

At next step 112, it is determined whether the square of the variance value calculated at the step 110 is smaller than a predetermined value S. When the square of the variance is less than the predetermined value S (i.e., an affirmative determination) the operation proceeds to step 114 and air pressure P is estimated from the average value $f_{AVE}$ of the resonance frequency calculated at the step 110 and according to the relationship between the resonance frequency and the air pressure shown in FIG. 4. Further, the relationship between the resonance frequency and air pressure is stored in the ROM of the ECU 12 or the like in the form of a map.

Meanwhile, when it is determined that the square of the variance value is not smaller than the predetermined value S in the step 112 (i.e., a negative determination), the operation proceeds to step 116 and the dynamic load radius is calculated based on the wheel speed from on the alternating current signals outputted from the respective wheel speed sensors 16A through 16D at that time point, and the air pressure P is estimated based on the calculated dynamic load radius.

That is, first, the alternating current signals respectively outputted from the wheel speed sensor 16A through 16D are subjected to waveform shaping to thereby form pulse signals Thereafter, based on the time interval between pulses wheel speeds of the respective tires is determined. Thereafter, an average value $V_{AVE}$ of the respective wheel speeds is calculated.

Next, the air pressure P is calculated based on the calculated wheel speed $V_{AVE}$.

$$P = (V_{AVE}/V) \times P_{ni} \qquad (3)$$

Here, "V" designates the wheel speed of the tire 20A based on the alternating current signal outputted from the wheel speed sensor 16A at that time point and "$P_{ni}$" designates standard constant tire air pressure.

Further, in Equation (3), the term $V_{AVE}/V$ designates a ratio equal to the ratio of dynamic load radius for the tire.

At next step 118, it is determined whether value of the air pressure P estimated by either of steps 114 and 116 is smaller than a predetermined threshold Pt. When the value is less than the predetermined threshold Pt (i.e., an affirmative determination), the operation proceeds to step 120 and a control signal for operating the warning device 14 is output. After emitting an alarm indicating to a passenger of the vehicle that the tire air pressure is abnormal, the tire air pressure estimation processing is finished. When the value is not smaller than the predetermined threshold Pt (i.e., a negative determination), it is determined that the tire air pressure is normal and the tire air pressure estimation processing is finished without executing the processing of the step 120.

A component for executing the processing of step 100 in the tire air pressure estimating apparatus 10 corresponds to an extracting component of the invention; a component for executing the processing of step 114 corresponds to a first estimating component of the invention; a component for executing the processing of step 116 corresponds to a deriving component; and a second estimating component of the invention and a component for executing the processing of step 112 corresponds to a switching component of the invention.

As has been explained above in detail, in the tire air pressure estimating apparatus 10 according to the first embodiment, estimation of the tire air pressure based on the resonance frequency and estimation of the tire air pressure based on the dynamic load radius, are applied for selective switching in accordance with the variance value of the resonance frequencies at a plurality of time points. Therefore, regardless of the various elements to be mounted to a vehicle, the tire air pressure can be estimated with high accuracy from operation at low to high speeds.

Further, although according to the first embodiment, an explanation has been given for applying the variance value of a plurality of the resonance frequencies as a statistic value, the invention is not limited thereto. For example, there can be an alternative embodiment where a bias or a kurtosis is applied as the statistic value of a plurality of resonance frequencies.

Figure 5A:
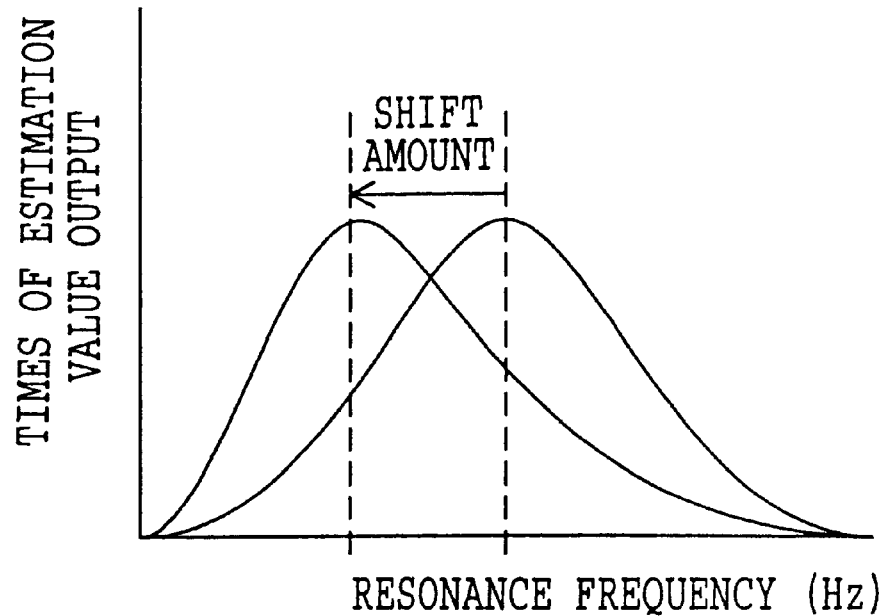
FIGS. 5A and 5B are graphs provided for an explanation of another mode of the first embodiment.
Figure 5B:
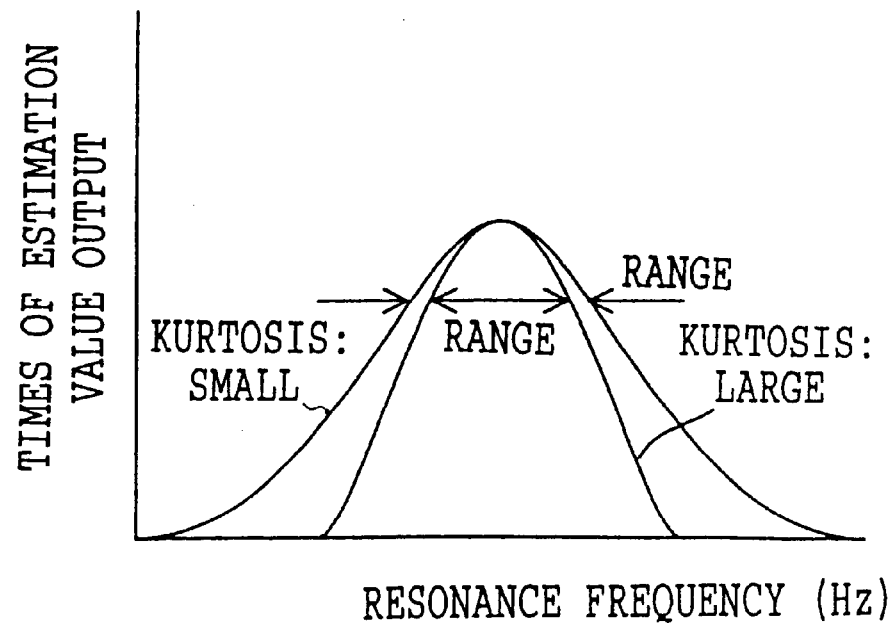

Here, the bias is a degree in accordance with a shift amount from a normal distribution in a histogram of the resonance frequency as shown by FIG. 5A. The kurtosis is a pointed degree of the normal distribution in the histogram of the resonance frequency as shown by FIG. 5B. In this case, an effect similar to that of the first preferred embodiment can be achieved.

(Second Embodiment)

An explanation will be given as follows of a second preferred embodiment of the invention. In this regard, the physical construction of the tire air pressure estimating apparatus 10 according to the second embodiment is similar to that of the tire air pressure estimating apparatus 10 according to the first embodiment (see FIG. 1) Therefore, an explanation thereof will be omitted here.

Figure 6A:
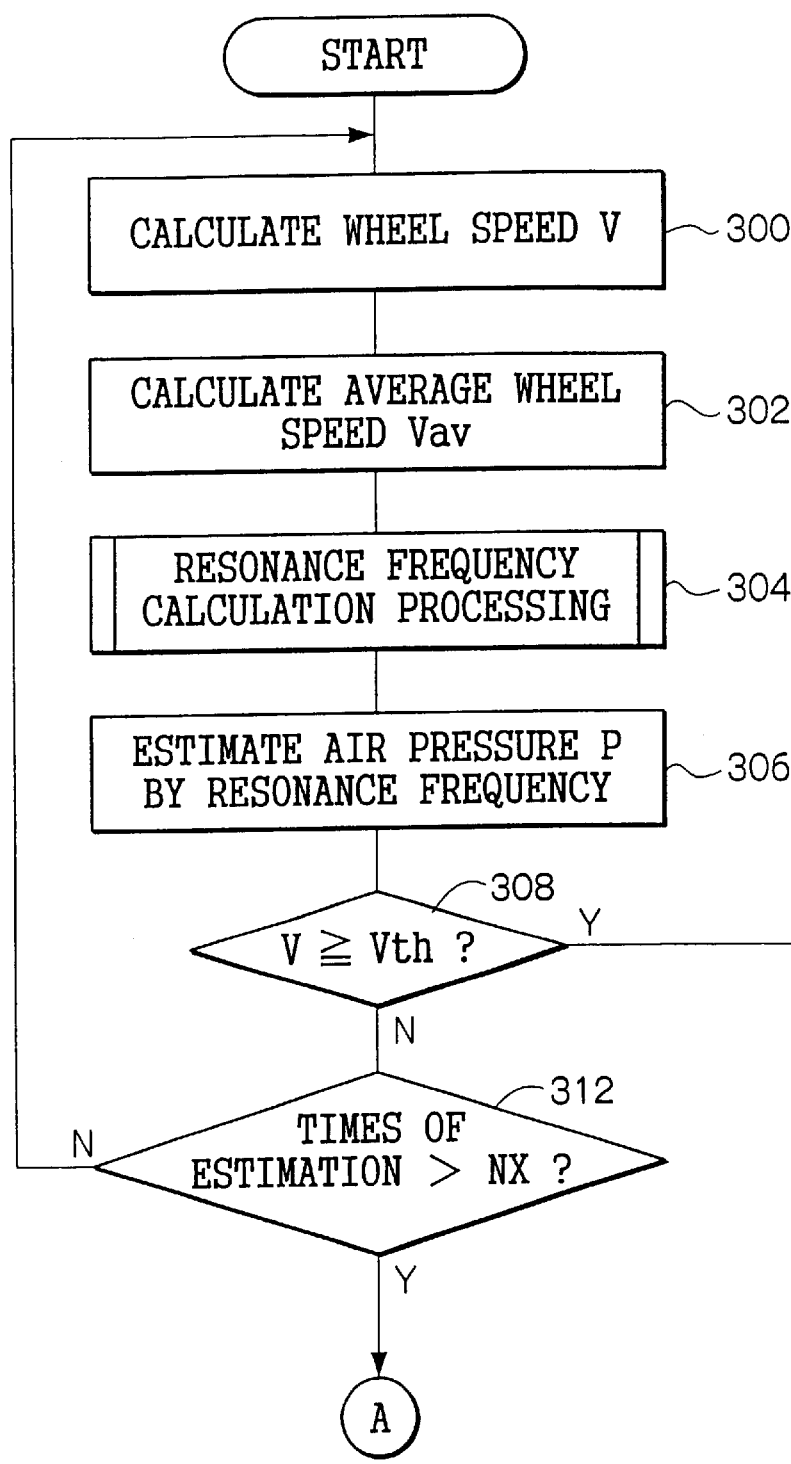
FIGS. 6A and 6B are flowcharts showing a flow for processing of a tire air pressure estimation processing program executed by the tire air pressure estimating apparatus 10 according to a second preferred embodiment.
Figure 6B:
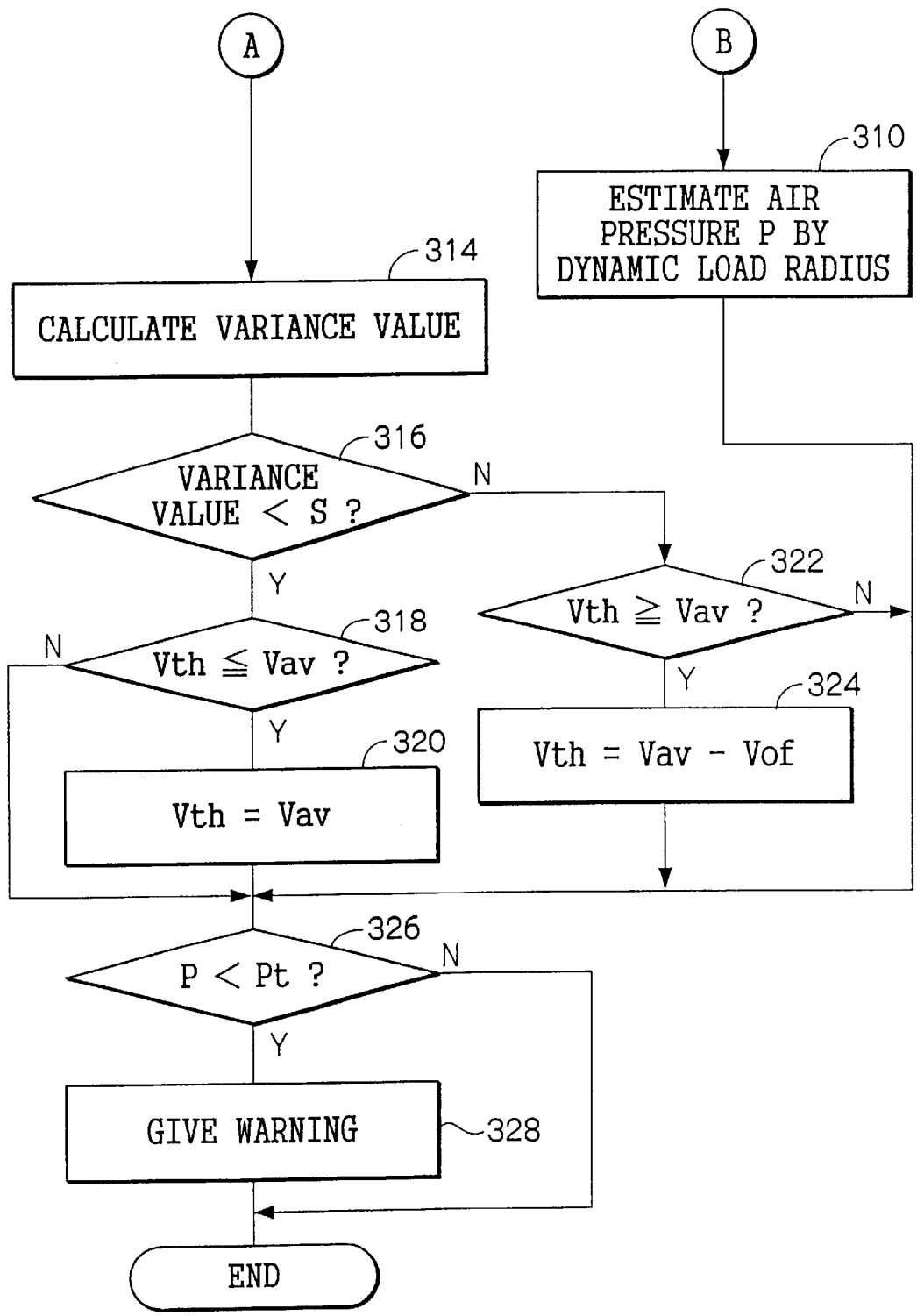

Instead, an explanation will be given of operation of the tire air pressure estimating apparatus 10 according to the second embodiment with reference to FIGS. 6A and 6B as follows. FIGS. 6A and 6B are flowcharts showing flow of a tire air pressure estimation processing program reiteratively executed by the CPU of ECU 12 at predetermined time intervals with the program previously stored in ROM of ECU 12. As ECU 12 executes similar processing each of tires 20A through 20D and, an explanation will be given here only of the processing for the tire 20A.

First, at step 300, the alternating current signal outputted from the vehicle speed sensor 16A is subjected to waveform shaping to thereby form pulse signals and Thereafter, based on time interval between pulses the wheel speed V is calculated. The vehicle speed V normally includes a number of high frequency components including frequency components of vibration of the tire.

At next step 302, there an average wheel speed Vav is calculated, which is an average of the vehicle speeds V which have been calculated at the step 300 until that time. At next step 304, resonance frequency operation processing is executed similar to the resonance frequency operation processing according to the first embodiment (see FIG. 3), At next step 306, similar to the step 114 of the tire air pressure estimation processing program according to the first embodiment (see FIGS. 2A and 2B), the air pressure P of the tire is estimated based on the resonance frequency provided by the step 304.

At next step 308, it is determined whether the wheel speed V calculated at the step 300 is equal to or larger than the threshold Vth. When the vehicle speed V is equal to or larger than the threshold Vth (i.e., an affirmative determination), the operation proceeds to step 310 and similar to the step 116 of the tire air pressure estimation processing program according to the first embodiment, the air pressure is estimated based on the dynamic load radius of tire. Thereafter, the operation proceeds to step 326 and when the wheel speed V is not equal to or larger than the threshold Vth (i.e., a negative determination), the operation proceeds to step 312 without executing the processing of the step 310. With regard to the predetermined threshold Vth initially in executing the processing, the applicable wheel speed in correspondence with the vehicle speed with the resonance frequency in the frequency range of about 30 through 50 Hz, is difficult to detect in the power spectral level of the vehicle speed signal in a vehicle having standard various elements, provided by experiments or computer simulations.

At step 312, it is determined whether the number of times of estimating the air pressure P (here, the number of times of estimating the air pressure P by the resonance frequency) exceeds the predetermined value NX. When the number does not exceed the predetermined value (i.e., a negative determination), the operation returns to step 300. At a time point at which the number exceeds the predetermined value (time point of affirmative determination), the operation proceeds to step 314.

By iterative processing of step 300 through step 312, there are provided NX pieces of the resonance frequencies, and the average wheel speed Vav comprising the average value of the wheel speed V calculated during the time period of the iterative processing.

The air pressure P estimated by the dynamic load radius is provided at a time point at which the iterative processing has been finished, and when the last calculated vehicle speed V is equal to or larger than the predetermined threshold vth. The air pressure P estimated by the resonance frequency is provided when the lastly calculated wheel speed V is smaller than the predetermined threshold Vth.

At step 314, a variance value of NX pieces of the resonance frequencies is calculated similar to step 110 of the tire air pressure estimation processing program according to the first embodiment.

At next step 316, it is determined whether the variance value calculated at the step 314 is smaller than a predetermined value S. When the variance value is smaller than the predetermined value S (i.e., an affirmative determination), the operation proceeds to step 318 and it is determined whether the predetermined threshold Vth is equal to or smaller than the average wheel speed Vav. In the case of affirmative determination, the operation proceeds to step 320, and the predetermined threshold Vth is replaced by the average wheel speed Vav, Thereafter, the operation proceeds to step 326 and in the case of negative determination, the operation proceeds to step 326 without executing the processing of step 320.

Meanwhile, when it is determined that the variance value is not smaller than the predetermined value S at the step 316 (i.e., a negative determination), the operation proceeds to step 322 where it is determined whether the threshold Vth is equal to or larger than the average wheel speed Vav. In the case of affirmative determination, the operation proceeds to step 324, where the predetermined threshold Vth is replaced by a value produced by subtracting a predetermined offset value Vof from the average wheel speed Vav. Thereafter, the operation proceeds to step 326 and in the case of negative determination, the operation proceeds to step 326 without executing the processing of step 324.

That is, in the case where the variance value is less than the predetermined value S and the predetermined threshold Vth is the average wheel speed Vav, it is regarded that accuracy for estimating the air pressure by the resonance frequency is greater and the predetermined threshold Vth is replaced by the average wheel speed Vav. Thereby, the predetermined threshold Vth can be increased a value higher than therebefore. As a result, the operation permits easy a estimation of the air pressure based on the resonance frequency.

Meanwhile, when the variance value is the predetermined value S and the predetermined threshold Vth is the average wheel speed Vav, it is regarded that the accuracy for estimating the air pressure by the dynamic load radius is greater than that by the resonance frequency and the estimated threshold Vth is replaced by the value produced by subtracting the predetermined offset value Vof from the average wheel speed Vav. Thereby, the predetermined threshold Vth can be decreased a value lower than therebefore. As a result, the operation permits easy an estimation of the air pressure by the dynamic load radius. For as the predetermined offset value Vof, a fixed value or a value in accordance with the variance value is applicable. When the value in accordance with the variance value is applied, there is applicable a mode in which the greater the variance value, the greater the value provided for the predetermined offset value Vof.

At step 326, it is determined whether the value of the air pressure P estimated by either of the step 306 and the step 310 is less than the predetermined threshold Pt. When the value is smaller than the predetermined threshold Pt (i.e., an affirmative determination), the operation proceeds to step 328 and a control signal for operating the warning device 14 is output for emitting an alarm indicating to a passenger of the vehicle that the tire air pressure is abnormal, the tire air pressure estimation processing is finished. When the value is not less than the predetermined threshold Pt (i.e., a negative determination), it is regarded that the tire air pressure is normal and the tire air pressure estimation processing finishes without executing the processing of the step 328.

In the tire air pressure estimating apparatus 10, a component for executing the processing of step 304 corresponds to an extracting component of the invention; a component for executing the processing of step 306 corresponds to the first estimating component of the invention; a component for executing the processing of step 310 corresponds to the deriving component and the second estimating component of the invention; and a component for executing the processing of step 308 corresponds to an estimation switching component of the invention; and a component for executing the processing of step 316 through step 324 corresponds to a setting component of the invention.

As has been explained above in detail, in the tire air pressure estimating apparatus 10 according to the second embodiment, when the wheel speed V is less than the predetermined threshold Vth, the operation is switched for estimating the tire air pressure based on the resonance frequency. When the wheel speed V is equal to or greater than the predetermined threshold Vth, the operation is switched for estimating the tire air pressure based on the dynamic load radius and the predetermined threshold Vth is set based on the variance value of the resonance frequency. Accordingly, regardless of various elements to be mounted to the vehicle, the tire air pressure can be estimated with greater accuracy from operating at low to high speeds.

Further, in the tire air pressure estimating apparatus 10 according to the second embodiment, the predetermined threshold Vth increases or decreases in accordance with the variance value of the resonance frequency promoting robust performance.

(Third Embodiment)

For a third preferred embodiment, an explanation will be given as follows of an example of an alternative the second embodiment of the invention. In this regard, the physical structure of the tire air pressure estimating apparatus 10 according to the third embodiment is similar to the physical structure of the tire air pressure estimating apparatus 10 according to the first embodiment (see FIG. 1). Accordingly, an explanation thereof will be omitted here.

Figure 7A:
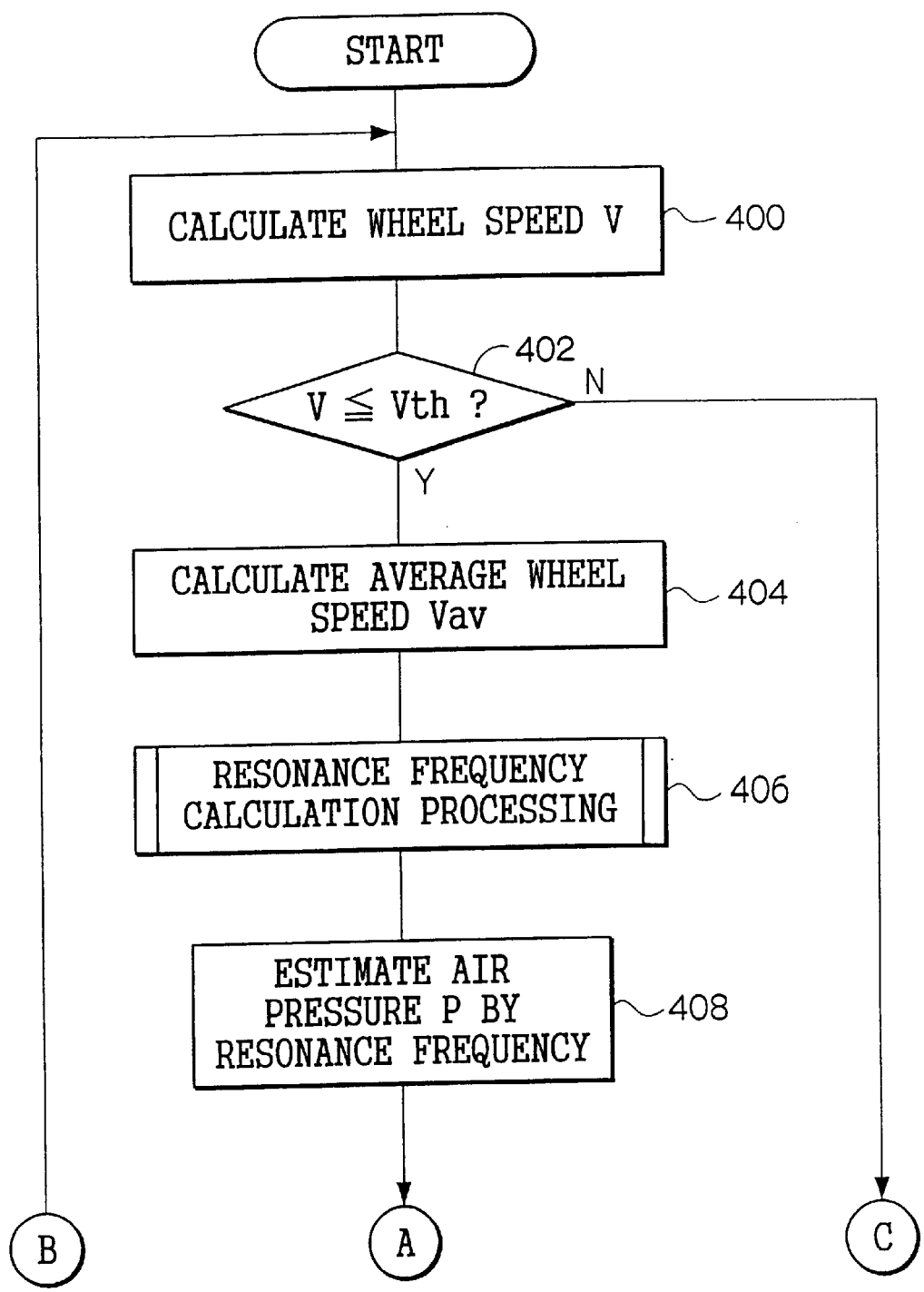
FIGS. 7A and 7B are flowcharts showing a flow for a processing of a tire air pressure estimation processing program executed by the tire air pressure estimating apparatus 10 according to a third preferred embodiment.
Figure 7B:
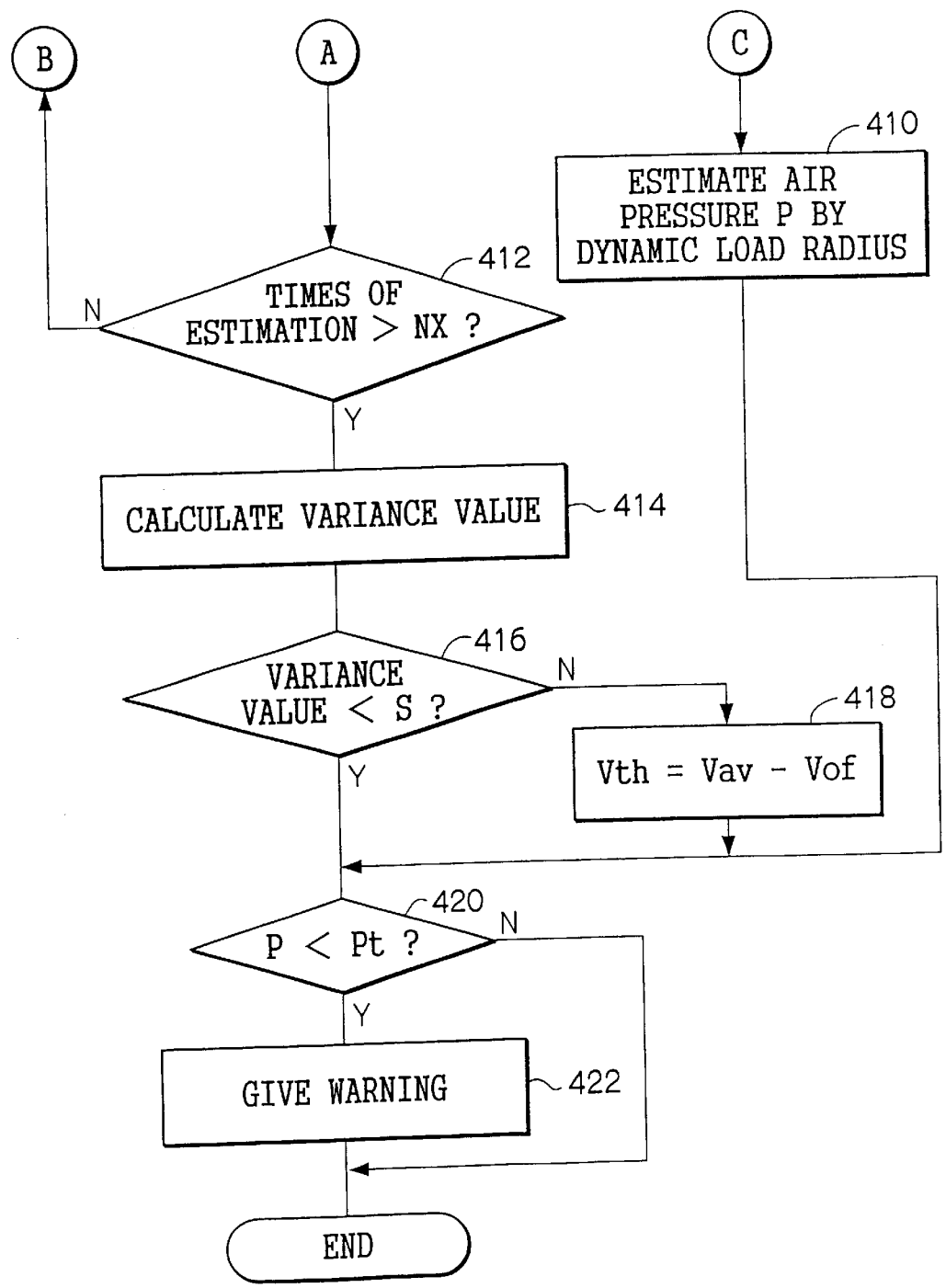

An explanation will be given of operation of the tire air pressure estimating apparatus 10 according to the third embodiment with reference to FIGS. 7A and 7B as follows. FIGS. 7A and 7B are flowcharts showing flow for a tire air pressure estimation processing program executed by the CPU of ECU 12 iteratively at predetermined time intervals with the program previously stored in ROM of ECU 12. Further, ECU 12 executes similar processing for the respective tires 20A through 20D and therefore, an explanation will be given here of only the processing for the tire 20A.

First, at step 400, an alternating current signal outputted from the vehicle speed sensor 16A is subjected to waveform shaping to thereby form pulse signals. Thereafter, based on time interval between the pulses the wheel speed v is calculated. The wheel speed V normally includes a number of high frequency components including frequency components of vibration of the tire.

At next step 402, it is determined whether the wheel speed V calculated at the step 400 is equal to or less than the predetermined threshold Vth. When the wheel speed V is equal to or less than the predetermined threshold Vth (i.e., an affirmative determination), the operation proceeds to step 404, where the average wheel speed Vav is calculated comprising an average value of the wheel speeds V which have been calculated at the step 400 until that time. At the next step 406, resonance frequency operation processing is executed similar to the resonance frequency operation processing according to the first embodiment (see FIG. 3). At next step 408, the air pressure P of the tire is estimated based on the resonance frequency provided by the step 406 similar to step 114 of the tire air pressure estimation processing program according to the first embodiment (see FIGS. 2A and 2B). Thereafter, the operation proceeds to step 412.

Meanwhile, when the vehicle speed V at the step 402 is not equal to or less than the predetermined threshold Vth (i.e., a negative determination), the operation proceeds to step 410, where the air pressure P is estimated based on the dynamic load radius of the tire similar to step 116 of the tire air pressure estimation processing program according to the first embodiment. Thereafter, the operation proceeds to step 420.

As the predetermined threshold Vth in initially executing the processing, wheel speed in correspondence with vehicle speed can be applied when it becomes difficult to detect resonance frequency in a frequency range of about 30 through 50 Hz in the power spectral level of the wheel speed signal of a vehicle having various standard various elements, which are provided by experiments or computer simulations.

At step 412, it is determined whether the number of times of estimating the air pressure P (the number of times of estimating the air pressure P by the resonance frequency) exceeds the predetermined value NX. When the number does not exceed the predetermined value NX (i.e., a negative determination), the operation returns to the step 400. The operation proceeds to step 414 at a time point at which the number exceeds the predetermined value NX (the time point of an affirmative determination).

By iterative processing of steps 400 through 412, there are provided NX pieces of the resonance frequencies and the average wheel speed Vav comprising the average value of the wheel speeds V which have been calculated during the time period of the iterative processing.

At a time point at which the iterative processing has been finished, and when the wheel speed V which has been calculated last, exceeds the predetermined threshold Vth, the air pressure P estimated by the dynamic load radius is provided. When the wheel speed V which has been calculated lastly, is equal to or less than the predetermined threshold Vth, the air pressure P estimated by the resonance frequency is provided.

At step 414, a variance value is calculated of NX pieces of the resonance frequencies similar to step 110 of the tire air pressure estimation processing program according to the first embodiment.

At next step 416, it is determined whether the variance value calculated at the step 414 is less than the predetermined value S. When the variance value is not less than the predetermined value S (i.e., a negative determination), the operation proceeds to step 418 and the predetermined threshold Vth is replaced by a value produced by subtracting the predetermined offset value Vof from the average wheel speed Vav. Thereafter, the operation proceeds to step 420 and when the variance value is less than the predetermined value S (i.e., an affirmative determination), the operation proceeds to step 420 without executing the processing of the step 418.

That is, by processing of steps 416 and 418, in the case of the variance value being less than the predetermined value S, the predetermined threshold Vth is not changed. When the variance value is the predetermined value S, it is regarded that estimation accuracy of the air pressure by the dynamic load average is greater than that of estimation by the resonance frequency and the predetermined threshold Vth is replaced by the value produced by subtracting the predetermined offset value Vof from the average wheel speed Vav. Thereby, the predetermined threshold Vth can be decreased to a value less than therebefore. As a result, the operation permits easy estimation of the air pressure by the dynamic load radius. Further, as the offset value Vof, there can be applied a fixed value or a value in accordance with the variance value and when the value in accordance with the variance value is applied, there is applicable a mode in which the greater the variance value, the greater the magnitude of the predetermined offset value Vof.

At the step 420, it is determined whether the value of the air pressure P by either of the step 408 and the step 410 is less than the predetermined threshold Pt. When the value is less than the predetermined threshold Pt (i.e., an affirmative determination), the operation proceeds to step 422 and a control signal for operating the warning device 14 is output for emitting an alarm representing that the tire air pressure is abnormal to a passenger of the vehicle. Thereafter, the tire air pressure estimation processing is finished. When the value is not less than the predetermined threshold Pt (i.e., a negative determination), it is regarded that the tire air pressure is normal and the tire air pressure estimation processing finishes without executing the processing of the step 422.

According to the tire air pressure estimating apparatus 10, a component for executing the processing of step 406 corresponds to an extracting component of the invention; a component for executing the processing of step 408 corresponds to the first estimating component of the invention; a component for executing the processing of step 410 corresponds to the deriving component and the second estimating component of the invention; a component for executing the processing of step 402 corresponds to the estimation switching component of the invention; and a component for executing the processing of step 416 and 418 corresponds to the setting component of the invention.

As has been explained above in detail, according to the tire air pressure estimating apparatus 10 according to the third embodiment, when the wheel speed V is equal to or less than the predetermined threshold Vth, the operation is switched to estimate the tire air pressure based on the resonance frequency, when the wheel speed V exceeds the predetermined threshold Vth, the operation switches to estimate the tire air pressure based on the dynamic load radius, and the predetermined threshold Vth is set based on the variance value of the resonance frequency. Therefore, regardless of various elements to be mounted to the vehicle, the tire air pressure can be estimated with high accuracy from operating at low to high speeds.

Further, in the tire air pressure estimating apparatus 10 according to the third embodiment, in operating at high speed, estimation of the air pressure by the resonance frequency is not executed. Therefore, in comparison with the tire air pressure estimating apparatus 10 according to the second embodiment, operation load can be reduced.

Although according to the second and third embodiment, an explanation has been given of the case of applying the variance value of the plurality of the resonance frequencies as the statistic value according to the second embodiment of the invention, the invention is not limited thereto, for example, there can be an alternative preferred embodiment in which bias or a kurtosis of the plurality of resonance frequencies is applied as the statistic value.

Figure 8:
FIG. 8 is a map showing an example of a relationship between a variance value and a predetermined threshold Vth.
Figure 9A:
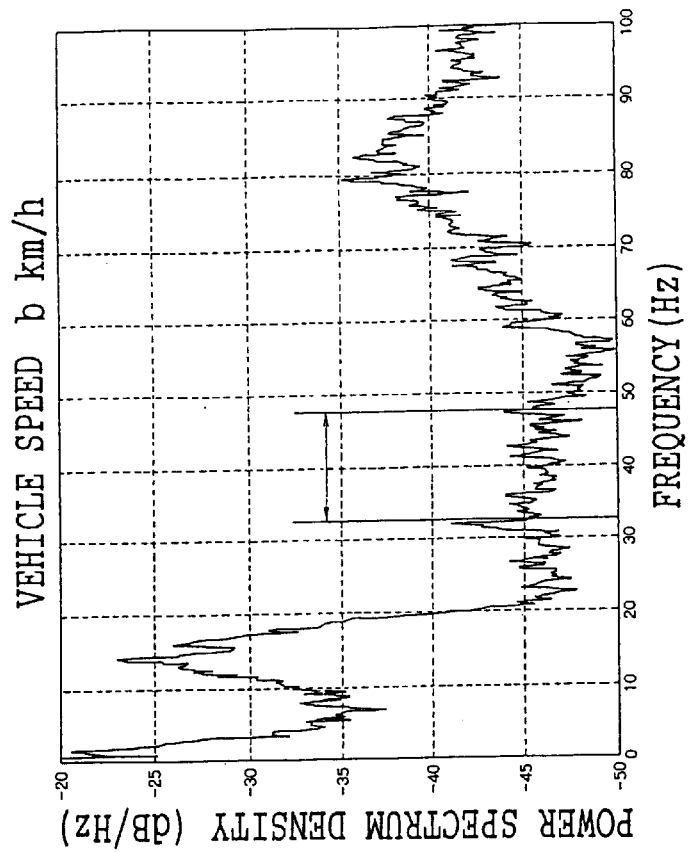
FIG. 9A is a diagram showing an example of a measured value of a power spectral level with respect to wheel speed signal in which the vehicle speed is at a middle speed of "a" km/h.
Figure 9B:
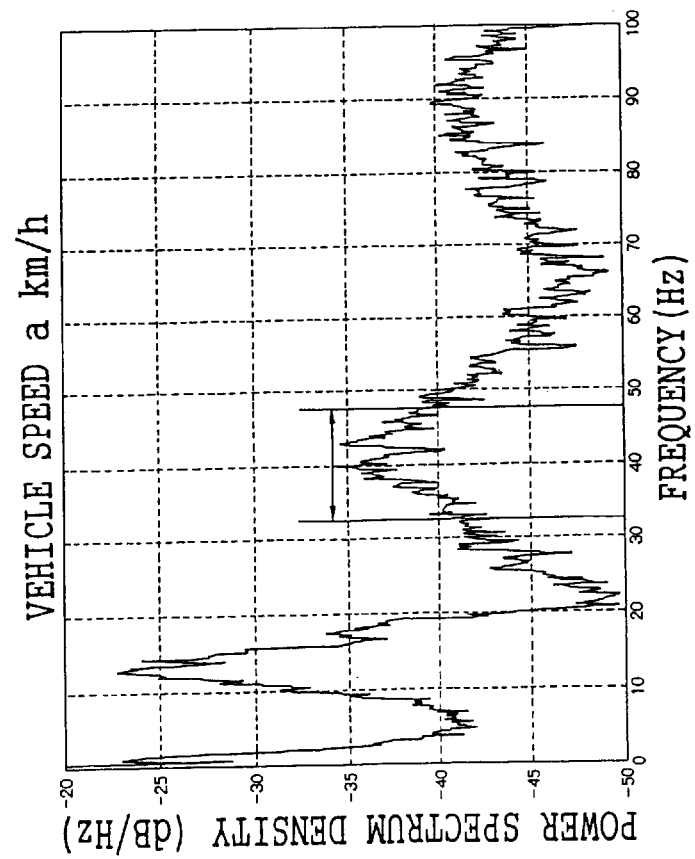
FIG. 9B is a diagram showing an example of a measured value of a power spectral level with respect to wheel speed signal in which the vehicle speed is at a high speed of "b" km/h.

Although according to the second and third embodiment, an explanation has been given of the case in which the predetermined threshold Vth is set by operation based on a large or small relationship of the variance value of the resonance frequencies with the predetermined value S, the invention is not limited thereto. For example, there can be an alternative embodiment in which a map representing a relationship between the variance value and predetermined threshold Vth shown by FIG. 8 is previously stored and the predetermined threshold Vth is set from a variance value from the map.

In this case, the predetermined threshold Vth can be set uniquely without executing an operation. Therefore, the processing time period can be decreased for setting the predetermined threshold Vth.

Although according to the second and third embodiment, an explanation has been given of the case in which the average wheel speed Vav is applied as a parameter in changing the predetermined threshold Vth, the invention is not limited thereto. For example, there can be an alternative embodiment in which in place of the average wheel speed Vav, the wheel speed having a high frequency of occurrence is applied. In this case, an effect similar to those of the second and third embodiment can be achieved.

Although according to the respective embodiment, an explanation has been given of the case in which the resonance frequency is extracted based on the wheel speed, the invention is not limited thereto. For example, in an alternative embodiment a spring constant of the tire can be extracted based on the wheel speed.

As a method of extracting the spring constant in this case, there can be exemplified an extracting method by a so-called disturbance observer system in which estimated disturbance is calculated based on the wheel speed by a disturbance observer and the spring constant of the tire is calculated based on the estimated disturbance. Further, the disturbance observer system is well known in the technical field. As various systems have been proposed conventionally a detailed explanation thereof will be omitted here.

As described above, the spring constant is the index having high correlation with the resonance frequency. Therefore, also in this case, an effect similar to that of the preferred embodiment can be achieved.

The method of deriving the resonance frequency shown in the respective embodiment is only an example and other methods of deriving the resonance frequency based on the wheel speed can be used (as examples, methods described in JP-A No. 6-297,923, JP-A No. 8-219,920 and the like).

According to the first embodiment of the tire air pressure estimating apparatus, the estimation of the air pressure by the first estimating component for estimating the tire air pressure based on the resonance frequency or the spring constant of the tire, and the estimation of the air pressure by the second estimating component for estimating the tire air pressure based on the dynamic load radius, are applied for selectively switching in accordance with a statistic value based on the resonance frequencies or the spring constant of the tire at a plurality of time points. Therefore, regardless of various elements to be mounted to the vehicle, an effect capable of estimating the tire air pressure with high accuracy from operating at low to high speeds is achieved.

According to the second embodiment of the tire air pressure estimating apparatus, the operation is switched to estimate the tire air pressure by the first estimating component for estimating the tire air pressure based on the resonance frequency or the spring constant of the tire when the wheel speed is less than the predetermined value. The operation switches to estimate the tire air pressure by the second component of estimating the tire air pressure based on the dynamic load radius when the wheel speed is equal to or greater than the predetermined value. The predetermined value is set based on the resonance frequency or the spring constant of the tire. Therefore, regardless of the various elements to be mounted to the vehicle, there an effect capable of estimating the tire air pressure with high accuracy from operating at low to high speeds is achieved.

What is claimed is:

1. An apparatus for estimating tire air pressure of a vehicle based on a wheel speed signal, the apparatus comprising an extracting component for extracting a resonance frequency or a spring constant of the tire based on a wheel speed signal including frequency components of vibration of the tire in operating the vehicle;

a first estimating component for estimating the tire air pressure based on the resonance frequency or the spring constant of the tire extracted by the extracting component;

a deriving component for deriving a dynamic load radius of the tire based on the wheel speed signal:

a second estimating component for estimating the tire air pressure based on the dynamic load radius derived by the deriving component; and a switching component for selectively switching estimation of the air pressure by the first estimating component and the second estimating component in accordance with a statistic value based on the resonance frequency or the spring constant of the tire at a plurality of time points, wherein the statistic value is any one of a variance value, a standard deviation value, bias, and a kurtosis of the resonance frequency or spring constant at the plurality of time points.

2. An apparatus for estimating tire air pressure of a vehicle based on wheel-speed signal, the apparatus comprising:

an extracting component for extracting a resonance frequency or a spring constant of the tire based on the wheel speed signal including frequency components of vibration of the tire in operating the vehicle:

a first estimating component for estimating the tire air pressure based on the resonance frequency or the spring constant of the tire extracted by the extracting component;

a deriving component for deriving a dynamic load radius based on the wheel speed signal:

a second estimating component for estimating the tire air pressure based on the dynamic load radius derived by the deriving component;

a wheel speed deriving component for deriving wheel speed based on the wheel speed signal;

an estimation switching component for switching from estimating the tire air pressure by the first estimating component when the wheel speed derived by the wheel speed deriving component is less than a predetermined value and switching to estimate the tire air pressure by the second estimating component when the wheel sDeed is at least equals the predetermined value; and a setting component for setting the predetermined value based on the resonance frequency or the spring constant of the tire, wherein the setting component sets the predetermined value in accordance with a statistic value based on the resonance frequency or the spring constant of the tire at the plurality of time points wherein the statistic value is any one of a variance value, a standard deviation value, bias, and a kurtosis of the resonance frequency or the spring constant at the plurality of time points.

3. A method of estimating tire air pressure comprising the steps of:

(a) extracting a resonance frequency or a spring constant of the tire based on a wheel speed signal including frequency components of vibration of a tire in operating a vehicle;

(b) estimating the tire air pressure based on the resonance frequency or the spring constant of the tire extracted;

(c) deriving a dynamic load radius of the tire based on the wheel speed signal:

(d) estimating the tire air pressure based on the dynamic load radius derived: and (e) selectively switching estimation of the air pressure by step (1) and a estimation of the air pressure using said steps of estimating tire air pressure based on resonance frequency or a spring constant, and the dynamic load radius in accordance with a statistic value based on the resonance frequency or the spring constant of the tire at a plurality of time points, wherein the statistic value is any one of a variance value, a standard deviation value, bias, and a kurtosis of the resonance frequency or the spring constant at the plurality of time points.

4. A method of estimating tire air pressure comprising the steps of:

(a) extracting a resonance frequency or a swing constant of the tire based on a wheel speed signal including frequency components of vibration of the tire in operating a vehicle; (b) estimating tire air pressure based on the resonance frequency or the spring constant of the tire extracted;

(c) deriving a dynamic load radius of the tire based on the wheel Speed signal;

(d) estimating the tire air pressure based on the dynamic load radius derived:

(e) deriving a wheel speed based on the wheel speed signal;

(f) switching from estimation of the tire air pressure by the step of estimating the tire air pressure based on the resonance frequency or the spring constant value when the wheel speed derived is less than a predetermined value and to estimation of the tire air pressure by the step of estimating the tire air pressure based on the dynamic load radius when the wheel speed at least equals the predetermined value; and (g) setting the predetermined value based on the resonance frequency or the spring constant of the tire, wherein the step of setting the predetermined value sets the predetermined value in accordance with a statistic value based on the resonance frequency or the spring constants of the tire at a plurality of time points, wherein the statistic value is any one of a variance value, a standard deviation value, bias, and a kurtosis of the resonance frequency or the spring constant at the plurality of time points.

* * * * *

UNITED STATES PATENT AND TRADEMARK OFFICE
CERTIFICATE OF CORRECTION

PATENT NO. : 6,711,508 B2
DATED : March 23, 2004
INVENTOR(S) : Kazuhiro Kamiya et al.

It is certified that error appears in the above-identified patent and that said Letters Patent is hereby corrected as shown below:

<u>Column 17,</u>
Line 28, change "sDeed" to -- speed --;

<u>Column 18,</u>
Line 2, start a new paragraph before (e) selectively;
Line 3, change "step (1)" to -- step (b) --;
Line 19, start a new paragraph before (b) estimating.

Signed and Sealed this

Eleventh Day of January, 2005

JON W. DUDAS
*Director of the United States Patent and Trademark Office*